United States Patent [19]

Nelson et al.

[11] Patent Number: 4,710,527
[45] Date of Patent: Dec. 1, 1987

[54] MALONATE-BASED LIGHT STABILIZERS FOR PLASTICS

[75] Inventors: Richard V. Nelson, Wilmington, Del.; John F. Stephen, West Chester, Pa.

[73] Assignee: ICI Americas Inc., Wilmington, Del.

[21] Appl. No.: 901,624

[22] Filed: Aug. 29, 1986

Related U.S. Application Data

[63] Continuation-in-part of Ser. No. 786,798, Oct. 11, 1985, abandoned.

[51] Int. Cl.$^4$ .............................................. C08K 5/34
[52] U.S. Cl. .................................... 524/98; 524/99; 524/100; 524/102; 524/103; 546/19; 546/188; 546/189; 546/190; 546/207
[58] Field of Search ................ 524/98, 99, 100, 102, 524/103; 546/19, 188, 189, 190, 207

[56] References Cited

U.S. PATENT DOCUMENTS

| | | | |
|---|---|---|---|
| 3,790,525 | 2/1974 | Murayama et al. | 260/45.8 NZ |
| 3,899,464 | 8/1975 | Murayama et al. | 260/45.8 NZ |
| 4,007,158 | 2/1977 | Murayama et al. | 524/99 |
| 4,105,626 | 8/1978 | Brunetti et al. | 260/45.8 NZ |
| 4,110,306 | 8/1978 | Minagawa et al. | 524/99 |
| 4,136,081 | 1/1979 | Minagawa et al. | 524/99 |
| 4,210,577 | 7/1980 | Minagawa et al. | 524/99 |
| 4,336,183 | 6/1982 | Nakahara et al. | 524/99 |
| 4,351,915 | 9/1982 | Kubota et al. | 524/99 |

FOREIGN PATENT DOCUMENTS 002299Z 1/1981 European Pat. Off. .

*Primary Examiner*—Morton Foelak
*Assistant Examiner*—Kriellion Morgan

[57] ABSTRACT

Malonate-based spiroacetals of polyalkylpiperidin-4-ones are useful light stabilizers for synthetic polymer resins such as polyolefins, and in particular, polypropylene.

13 Claims, No Drawings

MALONATE-BASED LIGHT STABILIZERS FOR PLASTICS

This is a continuation of co-pending application Ser. No. 786,798 filed on Oct. 11, 1985, now abandoned.

The invention pertains to polymeric compositions which are resistant to degradation when exposed to actinic radiation. In particular, it is directed to resins such as polypropylene stabilized with effective amounts of cyclic acetals of polyalkyl 4-oxopiperidine. The invention is further directed to a novel group of substances which are useful as additives for synthetic polymers by acting to retard photo-degradation and to a process for their manufacture.

Many synthetic organic polymers deteriorate rapidly when exposed to sunlight. To circumvent this rapid degradation many additives have been developed to stabilize these resins against the harmful radiation. These additives include hydroxybenzophenones, hydroxybenzotriazoles, organonickel complexes, and a number of compounds which incorporate a hindered amine, such as 2,2,6,6-tetraalkylpiperidine, that is substituted in the 4-position. However, because none of these compounds sufficiently satisfy the stabilization requirements of polymers in their wide variety of forms and applications, there remains a need for new substances which will be more fully satisfactory.

The polymer compositions of the invention are made by incorporation of an effective amount of novel acetals derived from a hindered piperidone compound. These compounds may be selected from those structure described by formula I in the Table of Structures which follows wherein:

$R^1$ is selected from hydrogen and an alkyl group of 1 to 5 carbon atoms such as methyl, ethyl, n-propyl, n-butyl, n-pentyl but is preferably hydrogen and methyl, and most preferably, hydrogen;

$R^2$ is selected from hydrogen, oxyl, hydroxyl, a straight or branched chain methylene-linked alkyl group from 1 to 18 carbon atoms, such as methyl, ethyl, octyl, octadecyl or 2-ethylhexyl, an alkanoyl group having 2 to 18 carbon atoms, such as acetyl, propanoyl, butanoyl, isopentanoyl, or stearoyl, an alkenyl group of 3 to 4 carbon atoms, an alkenoyl group having 3 to 6 carbon atoms, such as acryloyl, methacryloyl, crotonyl, 2,3-dimethylcrotonyl, an alkynyl group having 3 to 6 carbon atoms such as propanyl or 2-butynyl, a cyanomethyl group, 2,3-epoxypropyl group, an unsubstituted or substituted aralkyl group of 7 to 15 carbon atoms such as 3,5-di-tert-butyl-4-hydroxybenzyl, 3-tert-butyl-4-hydroxybenzyl, or 3-tert-butyl-4-hydroxy-5-methyl-benzyl, a group $-CH_2CH(OR^4)-R^5$, and a group of the formula

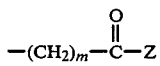

wherein m is either 0 or 1 and Z is a group selected from $-OR^6$; $-N(R^7)(R^8)$ and

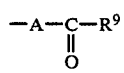

and when m is zero, Z may be a group $-C(O)-OR^{10}$, $R^3$ is selected from an alkyl group of 1 to 18 carbon atoms such as those of $R^2$ and a group of the formula II, $R^4$ from hydrogen, an aliphatic group of 1 to 18 carbon atoms such as those of $R^2$, an araliphatic group such as benzyl and phenethyl, and an aliphatic acyl group of 2 to 18 carbon atoms such as those of $R^2$, $R^5$ is selected from hydrogen, an alkyl group of 1 to 16 carbon atoms such as those of $R^2$, and phenyl;

$R^6$ is selected from an alkyl group of 1 to 18 carbon atoms, a cycloalkyl group of 5 to 12 carbon atoms such as cyclopentyl, cyclohexyl, cyclooctyl, and cyclododecyl, allyl, benzyl, phenyl, and a group of formula II wherein $R^1$ and $R^2$ are as described above;

$R^7$ and $R^8$, same or different, are selected from hydrogen, an alkyl group having 1 to 8 carbon atoms such as methyl, ethyl, hexyl, a cycloalkyl group having 5 to 12 carbon atoms such as those of $R^6$, aryl groups having 6 to 10 carbon atoms such as 4-methylphenyl, 2-methylphenyl, 4-butylphenyl, and aralkyl groups having 7 to 15 carbon atoms such as benzyl, o, m, and p-alkylsubstituted benzyl, and phenethyl, and, $R^7$ and $R^8$ together with the nitrogen atom to which they are attached can form a 5 to 7-membered ring such as pyrrolidine, piperidine and homopiperidine;

A is selected from a straight or branched chain alkylene group of 1 to 12 carbon atoms, phenylene and a group $-NH-R^{11}-NH-$ where $R^{11}$ is selected from an alkylene group of 2 to 18 carbon atoms, either straight chained or branched, a cycloalkylene group having 5 to 18 carbon atoms, an arylene group having 6 to 18 carbon atoms, and an aralkylene group having 7 to 18 carbon atoms, and $R^9$ is a group of the formula III, $R^{10}$ is selected from $C_{1-18}$ alkyl such as those of $R^2$, phenyl or benzyl, and is preferably $C_{1-2}$ alkyl, X is either $-O-$ or $-NR^{12}$ where $R^{12}$ is selected from hydrogen or an alkyl group of 1 to 8 carbon atoms such as methyl, ethyl, butyl or octyl.

The acetals of formula I may be prepared in a single or multi-step process depending on the nature of $R^2$ and $R^3$. These acetals can be prepared from the reaction of a diol of the formula $(HOCH_2)_2C-(CO_2R^3)_2$ with a 4-oxopolyalkyl piperidine of the formula IV using a suitable acid catalyst and a suitable solvent as generally known in the art for the preparation of acetals. Examples of suitable acid catalysts are numerous, however, without introducing any limitations are mentioned p-toluenesulfonic acid and methanesulfonic acid. Examples of suitable solvents are cyclohexane and benzene. Although $R^3$ may be any alkyl group of 1 to 18 carbon atoms for this reaction it is preferred that $R^3$ be ethyl.

The preparation of the preferred material has been described in the literature, i.e., Organic Synthesis Collective Vol. V, 381–383 (1973) and the material is commercially available. This procedure requires reacting diethylmalonate with aqueous formaldehyde in the presence of a catalyst such as potassium bicarbonate and thereafter isolating the product by salting out and solvent extraction.

The reaction of 2,2,6,6-tetraalkyl-4-piperidones with dihydroxy substances to from the corresponding acetal derivatives is well-known and techniques similar to those described in U.S. Pat. No. 3,790,525; 3,899,464; 4,007,158; 4,105,626; and EP No. 22,997 may be employed. Of particular interest as a starting component is 2,2,6,6-tetramethyl-4-piperidone. Preparative procedures for this ketone may be found throughout the literature and in U.S. Pat. No. 4,105,626, Column 9.

Specifically the compound is prepared by the reaction of ammonia with acetone.

The preparation of other polyalkylpiperidin-4-ones of formula IV can be prepared by reaction of ammonia with an aliphatic ketone such as methyl ethyl ketone. This procedure has been described by W. Traube in Chem, Ber. 41,777 (1908).

Compounds of the formula IV which carry other alkyl substituents in the 2-position and the 6-position can be prepared in a two step process following the procedures outlined in Helv. Chim. Acta 30,1114(1947) and Monatsh.Chem. 88,464(1957), followed by hydrolysis of the resulting pyrimidine.

The acetalization reaction is generally carried out in a refluxing solution of a water-immiscible solvent at a temperature of about 80° C. in the presence of an acid catalyst. Solvents which work well are cyclohexane and benzene as well as others that may be useful. Acid catalysts which are commonly utilized are organic acids such as methanesulfonic acid, paratoluenesulfonic acid and others which are considered useful.

The acetal resulting from reaction of the diethyl bis(hydroxymethyl)malonate and the appropriate piperidin-4-one is generally isolated by solvent extraction and after concentration can be purified by either distillation or crystallization.

The diethyl spiroacetal can be used as a starting material for the second step in the process. Higher molecular weight monomeric esters and amides can be prepared by reaction of the diethyl spiroacetal, neat or in solution, with higher molecular weight monofunctional alcohols, amines or mixtures thereof using a basic catalyst like lithium amide or titanium tetraisopropoxide. Examples of suitable solvents are ligroine and toluene. The products may be separated from solvent solution and are generally purified by the trituration or crystallization or any other suitable procedure.

The 4-hydroxypolyalkylpiperidines and the 4-aminopolyalkylpiperidines used to convert the acetals into the compounds of the invention are know from German Patent 2,352,658 and U.S. Pat. No. 3,684,765. In general, the 4-hydroxy compounds are prepared from the corresponding 4-oxopiperidines by reduction via catalytic hydrogenation over Raney Nickel and the 4-amino compounds are synthesized via a reductive amination using ammonia or the particular primary amine of interest.

The introduction of an alkyl, alkenyl alkynyl, aralkyl and 2,3-epoxypropyl group can be achieved by reaction of the initially prepared acetal containing the free N—H of the polysubstituted piperidine with suitable halides like methyl iodide, ethyl bromide, propyl bromide, dodecyl chloride, and octadecyl chloride; allyl bromide, methallyl chloride, butenyl chloride, propargyl bromide, benzyl chloride, phenethyl bromide, and epichlorohydrin. The generated hydrogen halide can be scavenged by the addition of an inorganic base such as carbonate or hydroxide or by the addition of an organic amine such as triethylamine to the reaction mixture.

An alternative way of preparing of the compounds of the invention which contain a 1-alkyl, 1-alkenyl, 1-alkynyl, 1-aralkyl, or 1-[2,3-epoxypropyl]group, especially when the desired invention compound is an ester, is to prepare the 1-substituted polyalkylpiperidin-4-ol as described in U.S. Pat. No. 4,014,887 and perform the transesterification in the manner as stated previously.

The introduction of an alkanoyl or an alkenoyl group can be performed by acylation of the parent N—H compound using the suitable acid halide or, when convenient, the acid anhydride. If the acid halide is used the generated hydrogen halide can be scavenged in the same manner as stated previously. Examples of such groups are acetyl chloride, propionyl chloride, hexanoyl chloride, dodecanoyl chloride, octadecanoyl chloride, acetic anhydride, and propionic anhydride, malonyl chlorile, succinyl chloride, and adipoyl chloride.

For the compounds when $R^2$ is the group —$CH_2CH(OR^4)$—$R^5$ the substituent can be introduced by reaction of the parent N—H compound with the corresponding alkylene oxide such as ethylene oxide, propylene oxide and styrene oxide. The resulting hydroxy compound can be acylated in the manner commonly known in the art using the suitable acid halide and can be alkylated by generating the alkoxide using a base like sodium hydride and treating it with the desired alkyl or aralkyl halide.

When $R^2$ is the group —$(CH_2)_m$COZ and m is zero the appropriate group can be attached by reacting the parent N—H compound with a chloroformate such as methyl chloroformate, ethyl chloroformate, allyl chloroformate, hexylchloroformate, decyl chloroformate, octadecyl chloroformate, and phenyl chloroformate. The preparation of the oxamide half esters can be achieved by reaction of the parent N—H compound with the oxalyl chloride monomethylester and oxalyl chloride monoethylester and scavenging the generated hydrogen chloride with a base as stated previously.

For preparation of the corresponding ureas the parent N—H compound can be treated with the suitable carbamyl halide such as methyl carbamyl chloride, ethyl carbamyl chloride, butyl carbamyl chloride, phenyl carbamyl chloride, dimethyl carbamyl chloride, diethylcarbamyl chloride, dihexylcarbamyl chloride, pyrrolidinyl carbamyl chloride, piperidine carbamyl chloride, and homopiperidine carbamyl chloride. Alternatively, the ureas can be prepared by treating the parent N—H compound with the suitable isocyanate. The bis-ureas can be prepared using the suitable disocyanate.

Compounds of formula I wherein $R^2$ is the oxyl radical are obtainable from the corresponding N—H compounds by oxidation with a peroxide such as hydrogen peroxide in the presence of a catalyst like sodium tungstate or with percarboxylic acids like metha-chloroperoxybenzoic acid.

When $R^2$ is the group —$(CH_2)_m$—COZ and m is 1 the appropriate group can be attached by reacting the parent N—H compound with an ester of chloroacetic acid such as methyl chloroacetate, ethyl chloroacetate, cyclohexylchloroacetate, ethyl chloroacetate, cyclohexylchloroacetate, benzyl chloroacetate, allyl chloroacetate and phenyl chloroacetate.

The compounds of this invention are effective light stabilizers for synthetic organic polymers The following examples are offered to demonstrate but not limit the scope of the invention.

EXAMPLE 1

8,8,10,10-Tetramethyl-1,5-dioxa-9-azaspiro-[5,5]undecane-3,3-dicarboxylic acid, diethylester.

A mixture of triacetoneamine (25.1 grams, 0.14 mol), diethyl bis(hydroxymethyl)malonate (35.2 grams, 0.16 mol) and paratoluene sulfonic acid (30.4 grams, 0.16 mol) in 360 milliliters of cyclohexane was heated to reflux and the generated water was removed as condensate in a Dean-Stark trap. The mixture was stirred at reflux for 10 hours after which time an additional (17.6 grams 0.08 mol) of malonate was added. After an additional 18 hours at reflux the mixture was cooled to room temperature and the acid neutralized with 300 milliliters of aqueous potassium carbonate (55.2 grams, 0.4 mol). The layers were separated and the aqueous portion was washed with cyclohexane. The combined organic extracts after drying were concentrated under reduced pressure to yield an orange colored viscous liquid (about 52 grams). The crude product was distilled at reduced pressure to yield the above named spiroacetal (44.1 grams, 85%), b.p. 135°–140° C. at 0.15 mm.

Analysis calculated for: $C_{18}H_{31}NO_6$: 60.48% C, 8.74% H, 3.92% N; Found: 60.01% C, 8.78% H, 3.78% N.

EXAMPLE 2

6,8-Diethyl-7,8,10-trimethyl-1,5-dioxa-9-azaspiro-[5.5]undecane-3,3-dicarboxylic acid, diethyl ester This compound was prepared in a manner identical to the preparation of Example 1 with the substitution of 2,6-diethyl-2,3,6-trimethylpiperidin-4-one for 2,2,6,6-tetramethylpiperdin-4-one. The ketone was prepared as stated in U.S. Pat. No. 4,105,626, Column 12.

EXAMPLE 3

8,8,10,10-Tetramethyl-1,5-dioxa-9-azaspiro-[5.5]undecane-3,3-dicarboxylic acid, diester with 2,2,6,6-tetramethyl-4-piperidinol To a mixture containing 15.41 grams, (0.043 mol) of the product of Example 1 and 2,2,6,6-tetramethyl-4-piperidinol (13.56 grams, 0.86 mol) in 100 milliliters of ligroine (90°–100° C.) at reflux was added 100 mg of lithium amide as catalyst. The mixture was allowed to stir at reflux with a gentle stream of nitrogen passing over the surface of the reaction mixture for about 24 hours. The material was extracted and worked up by pouring the mixture into additional hot ligroine, removing the insolubles by filtration, concentrating the filtrate and allowing the mixture to crystallize. Isolation of the product by filtration yielded 18.64 grams (0.032 mol, 75% yield) of the above named compound m.p. 167.5°–169° C.

Analysis calculated for: $C_{32}H_{57}N_3O_4$: 66 29% C, 9.91% H, 7.25% N; Found: 66.25% C, 9.47% H, 7.48% N.

EXAMPLE 4

8,8,10,10-Tetramethyl-1,5-dioxa-9-azaspiro-[5.5]undecane-3,3-dicarboxylic acid, diester with 1,2,2,6,6-pentamethyl-4-piperidinol To a mixture of the compound of Example 1 (2.94 grams, 8.2 millimole) and 1,2,2,6,6-pentamethyl-4-piperidinol (2.82 gram, 16.4 mmol) in about 50 ml of ligroine at reflux (90°–110° C.) was added lithium amide (38 mg) as catalyst. A general stream of nitrogen was passed over the surface of the mixture for 20 hours before pouring the hot mixture into additional hot ligrioine and subsequently filtering the solution. The filtrate was concentrated and allowed to crystallize to yield 3.2 gram (64% yield) of the named compound as a white solid, mp 83°–87° C.

Analysis calculated for: $C_{34}H_{61}N_3O_6$: 67.18% C, 10.12% H, 6.91% N, Found: 66.42% C, 10.27% H, 6.46% N.

EXAMPLE 5

9-Butyl 8,8,10,10-tetramethyl-1,5-dioxa-9-azaspiro-[5.5]undecane-3,3-dicarboxylic acid, diester with 1-butyl-2,2,6,6-tetramethylpiperidin-4-ol A mixture of the product of Example 3 (5.8 g, 10 mmol) was treated with 4.5 g (33 mmol) of 1-bromobutane in 25 ml of tetrahydrofuran containing triethylamine (36 mmol). The mixture was heated at reflux for 72 hours whereupon it was cooled, concentrated and the residue was partitioned between dichloromethane and water. The organic solution was dried (sodium sulfate) and concentrated. Purification of the residue yielded the desired product as evidenced by NMR and mass spectroscopy.

In the same manner as stated for the preparation of Example 5 the following are prepared:

(COMPOUND/ORGANIC HALIDE)

9-Allyl-8,8,10,10-tetramethyl-1,5-dioxa-9-azaspiro-[5.5]undecane-3,3-dicarboxylic acid, diester with 1-allyl-2,2,6,6-tetramethylpiperidin-4-ol/allyl bromide 9-Docecyl-8,8,10,10-tetramethyl-1,5-dioxa-9-azaspiro-[5.5]undecane-3,3-dicarboxylic acid, diester with 1-docecyl-2,2,6,6-tetramethylpiperdin-4-ol/1-bromododecane 9-Propargyl-8,8,10,10-tetramethyl-1,5-dioxa-9-azaspiro-[5.5]undecane-3,3-dicarboxylic acid, diester with 1-propargyl-2,2,6,6-tetramethyl-piperidin-4-ol/propargyl bromide 9-[2,3-Epoxypropyl]-8,8,10,10-tetramethyl-1,5-dioxa-9-azaspiro-[5.5]undecane-3,3-dicarboxylic acid, diester with 1-[2,3-epoxypropyl]-2,2,6,6-tetra-methylpiperidin-4-ol/epichlorohydrin 9-[1-Ethoxycarbonylmethyl]-8,8,10,10-tetramethyl-1,5-dioxa-9-aspiro-[5.5]undecane-3,3-dicarboxylic acid, diester with 1-ethoxycarbonylmethyl-2,2,6,6-tetranethylpiperidin-4-ol/ethyl chloroacetate 9-[1-Dodecyloxycarbonylmethyl]-8,8,10,10-tetramethyl-1,5-dioxa-9-azaspiro-[5.5]undecane-3,3-dicarboxylic acid, diester with 1-dodecyloxycarbonyl-methyl-2,2,6,6-tetramethylpiperidin-4-ol/dodecyl chloroacetate 9-[1-Cyclohexyloxycarbonylmethyl]-8,8,10,10-tetramethyl-1,5-dioxa-9-azaspiro-[5.5]undecane-3,3dicarboxylic acid, diester with 1-cyclohexyloxycarbonylmethyl-2,2,6,6-tetramethylpiperidin-4-ol/cyclohexyl chloroacetate 9-[1-Allyloxycarbonyl]-8,8,10,10-tetramethyl-1,5-dioxa-9-azaspiro[5.5]undecane-3,3-dicarboxylic acid, diester with 1-allyloxycarbonyl-2,2,6,6-tetramethylpiperidin-4-ol/allyl chloroformate 9-[1-Ethoxycarbonyl]-8,8,10,10-tetramethyl-1,5-dioxa-9-azaspiro[5.5]undecane-3,3-dicarboxylic acid, diester with 1-ethoxycarbonyl-2,2,6,6-tetramethylpiperidin-4-ol/ethyl chloroformate 9-[1-Phenyloxycarbonyl]-8,8,10,10-tetramethyl-1,5-dioxa-9-azaspiro[5.5]undecane-3,3-dicarboxylic acid, diester with 1-phenyloxycarbonyl-2,2,6,6-tetramethylpiperidin-4-ol/phenyl chloroformate

EXAMPLE 6

8,8,10,10-Tetramethyl-1,5-dioxa-9-azaspiro-[5.5]undecane-3,3-dicarboxylic acid, dioctadecyl ester To a mixture of the compound of Example 1 (5.71 g, 16.0 mmol) and 1-octadecanol (9.50 g, 35.0 mmol)

which was heated to 135° C. under a stream of nitrogen was added sodium methoxide (120 mg). The temperature was increased to 160°–170° C. and maintained for about 3 hours. Subsequently the mixture was cooled and an off-white solid was obtained (13 g, 100% recovery). This material was treated with hexane and ether to effect removal of the color and some purification, m.p. 54°–56° C.

Analysis calculated for: $C_{50}H_{95}NO_6$: 73.70% C; 12.24% H; 1.79% N; Found: 73.68% C; 11.48% H; 1.42% N.

EXAMPLE 7

9-Acetyl-8,8,10,10-tetramethyl-1,5-dioxa-9-azaspiro[5.5]undecane-3,3-dicarboxylic acid, diethyl ester A mixture containing 44.68 g (0.125 mol) of the product of Example 1 and 71.05 g (0.70 mol) of acetic anhydride was heated at reflux for 24 h. The solution was cooled, diluted with chloroform and washed with saturated sodium carbonate solution (4×200 ml) and then with water (2>200 ml). After drying with sodium sulfate and concentration, a brown solid was isolated. Recrystallization yield a white solid (40.0 g, 80% yield) melting at 75°–77° C.

Analysis calculated for: $C_{20}H_{33}NO_7$: 60.13% C; 8.33% H: 3.51% N; Found: 60.13% C; 8.39% H; 3.58% N.

EXAMPLE 8

9-Acetyl-8,8,10,10-tetramethyl-1,5-dioxa-9-azaspiro5,5]undecane-3,3-dicarboxylic acid, diester with 1,2,2,6,6-pentamethyl-4-piperidinol To a mixture of the compound of Example 7 (9.22 g, 23 mmol) and 1,2,2,6,6-pentamethyl-4-piperidinol (7.88 g, 46 mmol) in 100 milliliters of ligroine (90°–110° C.) at reflux was added the lithium amide (53 mg, 2.3 mmol) catalyst. The mixture was refluxed under a gentle stream of nitrogen for 5 h and was then diluted with ligroine. The catalyst was destroyed with glacial acetic acid and the mixture was filtered, decolorized and then concentrated to yield a white foam. Chromatographic purification yielded 5.95 g of the desired product (40% yield) as a white foam, m.p. 68°–70° C.

Analysis calculated for: $C_{36}H_{63}N_3O_7$: 66.53% C; 9.77% H; 6.47% N; Found: 65.99% C; 9.79% H; 6.42% N.

EXAMPLE 9

9-Acetyl-8,8,10,10-tetramethyl-1,5-dioxa-9-azaspiro[5,5]undecane-3,3-dicarboxylic acid, diester with 1-acetyl-1,2,2,6,6-tetramethyl-4-piperidinol A mixture of the compound of Example 3 (16.43 g, 28 mmol) and acetic anhydride (34.68 g, 340 mmol) in 50 ml of chloroform was heated at reflux for 21 h. The solution was cooled, diluted with chloroform and washed with saturated sodium carbonate solution (3×200 ml) and then with water (3×200 ml). Dried with sodium sulfate and concentrated. The resulting yellow oil was triturated with ether producing a white powder. Recrystallization from ethyl acetate yielded a white solid (12.33 g, 62% yield) with a melting point of 161.5°–163° C.

Analysis calculated for: $C_{38}H_{63}N_3O_9$: 64.65% C; 9.00% H; 5.95% N; Found: 64.51% C; 8.84% H; 5.84% N.

EXAMPLE 10

8,8,9,10,10-Pentamethyl-1,5-dioxa-9-azaspiro-[5.5]-undecane-3,3-dicarboxylic acid, diester with 1,2,2,6,6-pentamethyl-4-piperidinol To a mixture of 8,8,9,10,10-pentamethyl-1,5-dioxa-9-azaspiro-[5.5]undecane-3,3-dicarboxylic acid, diethyl ester, prepared from 1,2,2,6,6-pentamethyl-4-piperidone and diethyl bis(hydroxymethyl) malonate in a manner analogous to that of Example 3, (8.96 g, 24 mmol) and 1,2,2,6,6-pentamethyl-4-piperidinol (8.22 g, 48 mmol) in 100 ml of ligroine (90°–110° C.) at reflux was added the lithium amide (27 mg, 1.2 mmol) catalyst. A gentle stream of nitrogen was continued for 24 h. The mixture was diluted with ligroine and the catalyst was destroyed with glacial acetic acid. The solution was filtered and allowed to cool and crystallize. Recrystallization from ligroine yielded a white powder (7.93 g, 53% yield) melting at 111°–113° C.

Analysis calculated for: $C_{35}H_{63}N_3O_6$: 67.60% C; 10.21% H; 6.76% N; Found: 67.49% C; 10.24% H; 6.53% N.

This compound can also be prepared by the methylation of the compound of Example 3 using formaldehyde and formic acid.

EXAMPLE 11

9-Acryloyl-8,8,10,10-tetramethyl-1,5-dioxa-9-azaspiro [5.5]undecane-3,3-dicarboxylic acid, diester with 1-acryloyl-2,2,6,6-tetramethylpiperdin-4-ol To a solution of the product of Example 3 (5.80 g, 10 mmol) in 40 ml of tetrahydrofuran was added a solution of acryloyl chloride (3.0 g, 33 mmol) in 25 ml of tetrahydrofuran dropwise over a period of 20 minutes. Upon completion of the addition of the mixture was permitted to stir at ambient temperature for 24 hours. The mixture was diluted with ether, neutralized with aqueous sodium hydroxide and partitioned with water. The organic solution was dried (magnesium sulfate) and concentrated to yield the crude product. Trituration with ether/petroleum ether (35°–60° C.) yielded the product as a white solid. This material was characterized by NMR and mass spectroscopies.

In a manner identical to the procedure of Example 14 the following illustrative compounds can be prepared:
9-Hexanoyl-8,8,10,10-tetramethyl-1,5-dioxa-9-azaspiro[5.5]undecane-3,3-dicarboxylic acid, diester with 1-hexanoyl-2,2,6,6-tetramethylpiperidin-4-ol
9-Stearoyl-8,8,10,10-tetramethyl-1,5-dioxa-9-azaspiro[5.5]undecane-3,3dicarboxylic acid, diester with 1-stearoyl-2,2,6,6-tetramethylpiperidin-4-ol
9-Dimethylcarbamyl-8,8,10,10-tetramethyl-1,5-dioxa-9-azaspiro[5.5]undecane-3,3-dicarboxylic acid, diester with 1-dimethylcarbamyl-2,2,6,6-tetramethylpiperidin-4-ol
9-Diethylcarbamyl-8,8,10,10-tetramethyl-1,5-dioxa-9-azaspiro[5.5]undecane-3,3-dicarboxylic acid, diester with 1-diethylcarbamyl-2,2-6,6-tetramethylpiperidin-4-ol

EXAMPLE 12

9-Butylcarbamyl-8,8,10,10-tetramethyl-1,5-dioxa-9-azaspiro[5.5]undecane-3,3-dicarboxylic acid, diester with 1-butylcarbamyl-2,2,6,6-tetramethylpiperidin-4-ol To a solution of the product of Example 3 (5.80 parts) in 40 ml of tetrahydrofuran was added a solution of butyl isocyanate (3.12 parts) in 20 parts of tetrahydrofuran. The mixture was allowed to stir at ambient temperature for 24 hours where upon concentration of the mixture and purification of the crude reaction mixture yielded the desired product as demonstrated by NMR and mass spectroscopies.

Similarly the following compounds are prepared:

9-Cyclohexylcarbamyl-8,8,10,10-tetramethyl-1,5-dioxa-9-azaspiro[5.5]undecane-3,3-dicarboxylic acid, diester with 1-cyclohexylcarbamyl-2,2,6,6-tetramethylpiperidin-4-ol 9-Allyl carbamyl-8,8,10,10-tetramethyl-1,5-dioxa-9-azaspiro[5.5]undecane-3,3-dicarboxylic acid, diester with 1-allylcarbamyl-2,2,6,6-tetramethylpiperidin-4-ol

EXAMPLE 13

9-[2-Hydroxyethyl]-8,8,10,10-tetramethyl-1,5-dioxa-9azaspiro[5.5]undecane-3,3-dicarboxylic acid, diester with
1-[2-hydroxyethyl]-2,2,6,6-tetramethylpiperidin-4-ol To a mixture of the product of Example 3 (5.80 g, 10 mmol) in isopropanol was added ethylene oxide 66 g, 150 mmol). The mixture was charged in an autoclave and heated. Upon completion of the reaction the mixture was concentrated and purified to yield the desired product as indicated by NMR and mass spectroscopy.

Similarly can be prepared the products derived form propylene oxide and styrene oxide.

EXAMPLE 14

9-[2-Stearoyloxyethyl]-8,8,10,10-tetramethyl-1,5-dioxa-9-azaspiro[5.5]undecane-3,3-dicarboxylic acid, diester with
1-[2-stearoyloxyethyl]-2,2,6,6,-tetramethylpiperidin-4-ol The product of Example 13 (7.12 parts) was combined with stearoyl chloride (9.55 parts) and triethylamine (3.33 parts) in tetrahydrofuran. The mixture was stirred at ambient temperature for 18 hours before being partitioned between dichloromethane and water. The organic solution upon drying and concentration yielded the product as evidenced by NMR and mass spectroscopy.

EXAMPLE 15

9-Cyanomethyl-8,8,10,10-tetramethyl-1,5-dioxa-9-azaspiro[5.5]undecane-3,3-dicarboxylic acid, diester with 1-cyanomethyl-2,2,6,6-tetramethylpiperidin-4-ol A mixture of the product of Example 3 (5.80 parts) and acetone cyanohydrin (2.81 parts) and excess formaldehyde (37% aqueous) was heated at reflux for 18 hours. The mixture was cooled, basified and extracted with ether. The organic solution was dried (magnesium sulfate) and concentrated to yield the crude product. Purification yielded the desired product as evidenced by NMR and mass spectroscopy.

EXAMPLE 16

8,8,10,10-Tetramethyl-1,5-dioxa-9-azaspiro[5.5]undecane-3,3-dicarboxylic acid, diamide with
4-amino-2,2,6,6-tetramethylpiperidine To a mixture of the compound of Example 1 (3.57 parts) and 3.43 parts of 4-amino-2,2,6,6-tetramethylpiperidine in 30 ml of DMSO was added sodium hydride (0.5 parts). The mixture was heated to 100° C. and maintained for 12 hours. The crude reaction mixture was partitioned between ethyl acetate and water after cooling. The organic solution was dried (sodium sulfate) and concentrated. After subsequent purification the product was characterized by NMR and mass spectroscopy.

The spiroacetal derivatives of the invention are particularly useful as light stabilizers for synthetic polymers which undergo degradation in the presence of air and actinic radiation. As used herein polymers are intended to embrace polyolefins including homopolymers of olefins such as low density and high density polyethylene, polypropylene, polystyrene, polybutadiene, polyisoprene and the like; and copolymers of olefins with other ethylenically unsaturated monomers such as ethylene-propylene copolymer, ethylene-butylene copolymer, ethylene-vinyl acetate copolymer, styrene-butadiene copolymer, acrylonitrilestyrene-butadiene copolymer and the like; polyvinylchlorides and polyvinylidene chlorides including homopolymers of each of vinylchloride and vinylidine chloride, vinylchloride-vinylidene copolymers and copolymers of each vinylchloride and vinylidene chloride with vinyl acetate or other ethylenically unsaturated monomer; polyacetal as such polyoxymethylene and polyoxyethylene; polyesters such as polyethyleneterephthalate; polyamide such as 6-nylon, 6,6-nylon and 6,10-nylon and polyurethanes and polymers derived from α,β-unsaturated acids and derivatives thereof, polyacrylates and polymethacrylates, polyacrylic amides and polyacrylonitrile, as well as copolymers of acrylic acid and one or more of its derivatives with a melamine-formaldehyde resin.

Synthetic polymers have been widely utilized in the art in view of their excellent properties in various forms or shapes, for example, filaments, fibers, yarns, filament sheet, other molded articles and other molded articles made from latex and foam. However, these polymers have some drawbacks such as poor light and heat stabilities among others. Stated illustratively, polyolefins and polyurethane elastomers frequently tend to undergo severe deterioration when exposed to light such as sunlight or ultraviolet light and polyvinyl chloride and polyvinylidine chlorides frequently tend to deterioration when exposed to light such as sunlight or ultraviolet light and polyvinyl chloride and polyvinylidene chlorides frequently tend to deteriorate and become colored by the action of light and heat together with elimination of hydrogen chloride. Polyamides are also frequently subjected to photodegradation. For the purpose of stabilizing these synthetic polymers against such degradation, these have been proposed in the art a number of stabilizers. For example, in the case of polyolefins, benzotriazole and benzophenone compounds; for polyurethanes, phenol compounds and benzophenone compounds; and for polyvinylchlorides and vinylidene chlorides, lead salts such as basic lead silicate and trisilicate, lead maleate and organic tin compounds such as dibutyltinlaurate and dibutyltinmaleate.

The resin should have incorporated within an effective stabilizing amount of a compound described by formula I. The amount will depend upon the nature of the plastic and the amount of radiation to which the plastic will be subject. Generally an amount between about 0.01% and 5.0% by weight of the polymer is effective. Preferably they may be used in concentrations between 0.05 and 1% by weight.

In addition, the light stabilizers of formula I may be used with fillers and additional stabilizers including antioxidants, flame retardant stabilizers, anti-slipping and antistatic agents, supplemental light stabilizers, pigments, dyes, lubricants, etc.

Suitable antioxidants include those of the hindered phenol type such as 2,6-di-t-butyl-p-cresol; 4,4'-bis(2,6-di-t-butylphenol); 4,4'-bis(2,6-diisopropylphenol); 2,4,6-tri-t-butylphenol; 2,2'-thiobis(4-methyl-6-t-butylphenol); octadecyl-2(3',5'-di-t-butyl-4'-hydroxyphenyl)-propionate; pentaerythrityl tetrakis(3,5-di-t-butyl-4-hydroxyphenyl propionate; 1,3,5-tris(3',5'-di-t-butyl-4-hydroxybenzyl) isocyanurate; 1,3,5-tris((3',5'-di-t-butyl-4'-hydroxyphenyl)propionate) isocyanurate; 1,3,5-tris(3',5'-di-t-butyl-4'-hydroxybenzyl)-2,4,6-dimethylbenzyl)-s-triazine-2,4,6-(1H,3H,5H)-trione and esters of thiodipropionic acid such as dilaurylthiodipropionate and distearylthiodipropionate etc.; hydrocarbyl phosphites such as triphenyl phosphite, trinonyl phosphite, didodecyl pentaerythrityl diphosphite, diphenyldecyl phosphite, tris-(2,4-di-t-butylphenyl)phosphite, bis(2,4-di-t-butylphenyl)pentaerythritol diphosphite, etc, in combinations thereof.

Suitable supplemental light stabilizers include those of the benzotriazole class, such as 2-(2'-hydroxy-5-t-octylphenyl)benzotriazole; 2,(2'-hydroxy- 3',5'-di-t-butyl-phenyl)-5-chlorobenzotriazole; 2-(2'-hydroxy-5'-methylphenyl)benzotriazole; 2-(2'-hydrox-3'-t-butyl-5'-methylphenyl)-5-chlorobenzotriazole; 2-(2'-hydroxy-3',5'-di-t-amylphenyl)-benzotriazole; those of the hydroxybenzophenone type such as 2-hydroxy-4-methoxybenzophenone; 2-hydroxy-4-octyloxybenzophenone; 2,2'-dihydroxy-4,4'-di-methoxybenzophenone; hindered phenol esters, such as n-hexadecyl-3,5-di-t-butyl-4-hydroxybenzoate; and 2',4'-di-t-butyl-phenol-3, 5-di-t-butyl-4-hdyroxybenzoate; metal complexes such as nickel complexes of 2,2'-thiobis-(4-6-octylphenol), nickel butylamine complexes of 2,2'-thiobis(4-t-octylphenol); nickel dibutyl thiocarbamate; nickel salts of 4-hydroxy-3,5-di-t-butylbenzylphosphonic acid monoalkyl esters where alkyl is methyl, ethyl, propyl, butyl etc.; nickel complexes of to 2-hydroxy-4-methylphenyl undecylketoneoxime. Further illustrative examples of suitable antioxidants of supplemental light stabilizers can be found in columns 3 and 4 of U.S. Pat. Nos. 3,488,290 and 3,496,134.

EXAMPLE 17-25

In order to further illustrate the effectiveness of the above-described compounds as light stabilizers the previously described materials of Examples 1, 3, 4, 7 and 8, 9, 10 were each incorporated into a commercially available polypropylene resin manufactured by Hercules Corporation as PRO-FAX® 6301 Polypropylene Resin. The light stabilizers were incorporated with the polypropylene by solvent blending (methylene chloride) at concentrations of 0.25% by weight of the total resin composition and as a primary antioxidant stearyl beta-3,5-di-t-butyl-4-hydroxyphenylpropionate was used at a centration of 0.2%. The resin was then extruded at 200° C. and compression molded at 6,000 psi at 188° C. to produce films having thicknesses of 5 mils. A control film was produced by an identical procedure with the light stabilizer omitted. Each film was exposed to Xenon Arc in an Atlas Weather-o-meter until the infrared carbonyl absorption increased by 0.5, which is considered to be the failure point.

TABLE I

| Example No. | Stabilizer | Hours to Failure |
|---|---|---|
| 17 | Control | 300 |
| 18 | Example 1 | 1860 |
| 19 | Example 3 | 4400 |
| 20 | Example 4 | 3750 |
| 21 | Example 7 | 1150 |
| 22 | Example 8 | >4000 |
| 23 | Example 9 | 3020 |
| 24 | Example 10 | >4000 |

TABLE OF STRUCTURES

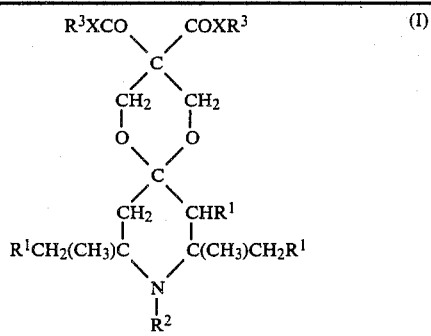

(I)

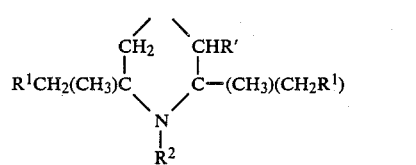

(II)

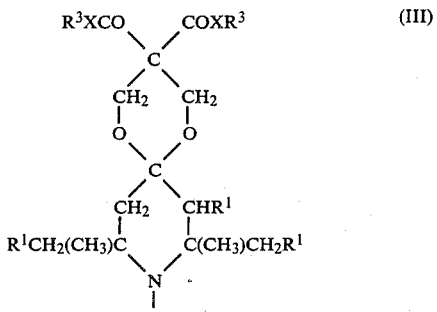

(III)

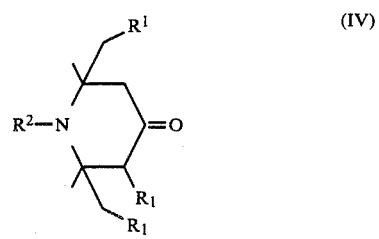

(IV)

What is claimed is:

1. A compound of the formula I wherein;

$R^1$ is selected from hydrogen and an alkyl group of 1 to 5 carbon atoms;

$R^2$ is selected from hydrogen, oxyl, hydroxyl, a methylene-linked alkyl group having from 1 to 18 carbon atoms, an alkanoyl group having 2 to 18 carbon atoms, an alkenyl group of 3 to 4 carbon atoms, an alkenoyl group having 3 to 6 carbon atoms, an alkynyl group having 3 to 6 carbon atoms, a cyanomethyl group, a 2,3-epoxypropyl group, an aralkyl group of 7 to 15 carbon atoms, a group —CH$_2$CH(OR$^4$)—R$^5$, and a group of the formula $$-(CH_2)_m-\overset{O}{\underset{\|}{C}}-Z$$

wherein m is either zero or one and Z is a group selected from —OR$^6$; —N(R$^7$)(R$^8$) and $$-A-\underset{\underset{O}{\|}}{C}-R^9$$

and when m is zero, Z may be a group —C(O)—OR$^{10}$;

R$^3$ is selected from an alkyl group of 1 to 18 carbon atoms and a group of formula II, R$^4$ is selected from hydrogen, an aliphatic group of 1 to 18 carbon atoms, an araliphatic group, and an aliphatic acyl group of 2 to 18 carbon atoms, R$^5$ is selected from hydrogen, an alkyl group of 1 to 16 carbon atoms and phenyl, R$^6$ is selected from an alkyl group of 1 to 18 carbon atoms, a cycloalkyl group of 5 to 12 carbon atoms, and a group of formula II wherein R$^1$ and R$^2$ are as described above;

R$^7$ and R$^8$, are selected from hydrogen, an alkyl group having 1 to 8 carbon atoms, a cycloalkyl group having 5 to 12 carbon atoms, an aryl group having 6 to 10 carbon atoms, and an aralkyl group having 7 to 15 carbon atoms, R$^7$ and R$^8$ together with the nitrogen atom to which they are attached can form a 5 to 7-membered ring selected from pyrrolidine, piperidine and homopiperidine;

A is selected from an alkylene group of 1 to 12 carbon atoms, phenylene, and a group —NH—R$^{11}$—NH— where R$^{11}$ is selected from an alkylene group of 2 to 18 carbon atoms, a cycloalkylene group having 5 to 18 carbon atoms, an arylene group having 6 to 18 carbon atoms, and an aralkylene group having 7 to 18 carbon atoms, and R$^9$ is a group of the formula III;

R$^{10}$ is selected from an aliphatic group of 1 to 18 carbon atoms, phenyl and benzyl, X is either —O— or —NR$^{12}$— where R$^{12}$ is selected from hydrogen or an alkyl group of 1 to 8 carbon atoms;

and wherein said formulas are as follows:

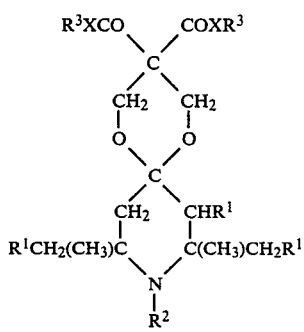

(I)

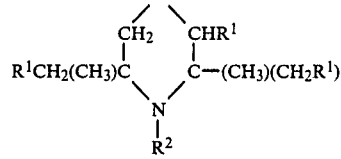

(II)

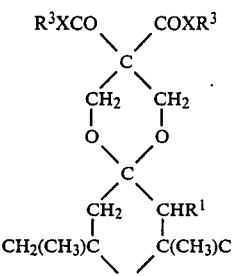

(III)

2. A compound of claim 1 wherein R$^1$ is hydrogen and X is —O—.

3. A compound of claim 2 which is 8,8,10,10-tetramethyl-1,5-dioxa-9-azaspiro[5.5]undecane-3,3dicarboxylic acid, diethyl ester.

4. A compound of claim 2 which is 8,8,10,10-tetramethyl-1,5-dioxa-9-azaspiro[5.5]undecane-3,3dicarboxylic acid, diester with 2,2,6,6-tetramethyl-4-piperidinol.

5. A compound of claim 2 which is 8,8,10,10-tetramethyl-1,5-dioxa-9-azaspiro[5.5]undecane-3,3dicarboxylic acid, diester with 1,2,2,6,6-pentamethyl-4-piperidinol.

6. A compound of claim 2 which is is 9-acetyl-8,8,10,10-tetramethyl-1,5-dioxa-9-azaspiro[5.5]undecane-3,3-dicarboxylic acid, diethyl ester.

7. A compound of claim 2 which is 9-acetyl-8,8,10,10-tetramethyl-1,5-dioxa-9-azaspiro[5.5]undecane-3,3-dicarboxylic acid, diester with 1,2,2,6,6-pentamethyl-4-piperdinol.

8. A compound of claim 2 which is 9-acetyl-8,8,10,10-tetramethyl-1,5-dioxa-9-azaspiro [5.5]undecane-3,3-dicarboxylic acid, diester with 1-acetyl-2,2,6,6-tetramethyl-4-piperidinol.

9. A compound of claim 2 which is 8,8,9,10,10-pentamethyl-1,5-dioxa-9-azaspiro[5.5]undecane-3,3-dicarboxylic acid, diester with 1,2,2,6,6-pentamethyl-4-piperidinol.

10. A synthetic polymer composition stabilized against light induced deterioration comprising an organic polymer normally subjected to deterioration by light, and from 0.01-5% by weight of a compound of the general formula of claim 1.

11. A composition of claim 10 wherein the organic polymer is a polyolefin homopolymer or copolymer.

12. A composition of claim 11 wherein said organic polymer is a homo or copolymer of polypropylene.

13. A process for the preparation of the compound of claim 3 which comprises heating the diethyl ester of bis(hydroxymethyl)malonate with a polyalkylated 4-piperidone in a refluxing solvent at a temperature less than about 100° C. in the presence of an acid catalyst.

* * * * *

UNITED STATES PATENT AND TRADEMARK OFFICE
CERTIFICATE OF CORRECTION

PATENT NO. : 4,710,527

DATED : December 1, 1987

INVENTOR(S) : Richard V. Nelson and John F. Stephen

It is certified that error appears in the above-identified patent and that said Letters Patent is hereby corrected as shown below:

Formulas II and III should be corrected in the Table of Structures, Column 12, and in the Claims, Column 14.

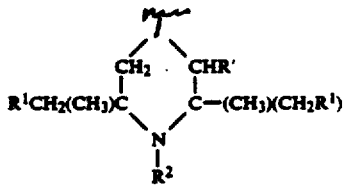

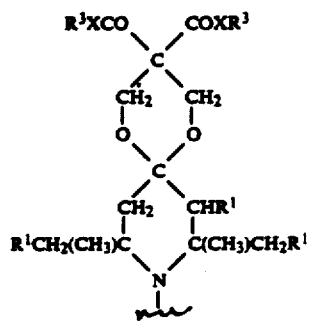

Signed and Sealed this

Nineteenth Day of April, 1988

Attest:

DONALD J. QUIGG

Attesting Officer      Commissioner of Patents and Trademarks